(12) United States Patent
Geske et al.

(10) Patent No.: US 8,105,790 B2
(45) Date of Patent: Jan. 31, 2012

(54) METHODS AND KITS FOR DETECTION OF THROMBOXANE A2 METABOLITES

(75) Inventors: F. Jon Geske, Broomfield, CO (US); Amy Whittier, Broomfield, CO (US); Daniel Tew, Ann Arbor, MI (US); Kirk M. Maxey, Ann Arbor, MI (US)

(73) Assignees: Corgenix Medical Corporation, Broomfield, CO (US); Cayman Chemical Company, Ann Arbor, MI (US)

( * ) Notice: Subject to any disclaimer, the term of this patent is extended or adjusted under 35 U.S.C. 154(b) by 26 days.

(21) Appl. No.: 12/750,092

(22) Filed: Mar. 30, 2010

(65) Prior Publication Data

US 2010/0227417 A1 Sep. 9, 2010

Related U.S. Application Data

(62) Division of application No. 11/609,123, filed on Dec. 11, 2006, now Pat. No. 7,727,730.

(60) Provisional application No. 60/748,788, filed on Dec. 9, 2005, provisional application No. 60/793,428, filed on Apr. 19, 2006.

(51) Int. Cl.
*G01N 33/53* (2006.01)
(52) U.S. Cl. .......................... 435/7.1; 436/518
(58) Field of Classification Search ............ None
See application file for complete search history.

(56) References Cited

U.S. PATENT DOCUMENTS

| 5,047,354 | A | 9/1991 | Foegh et al. |
| 6,589,756 | B1 | 7/2003 | Barlow |
| 6,967,083 | B2 | 11/2005 | Ens |
| 7,727,730 | B2 | 6/2010 | Geske et al. |
| 2002/0037933 | A1 | 3/2002 | Basu et al. |
| 2011/0275789 | A1 | 11/2011 | Geske et al. |

OTHER PUBLICATIONS

Chiabrando et al. (Prostaglandins 1993 vol. 45, p. 401-411).*
Antithrombotic Trialists Collaboration (2002) "Collaborative Meta-Analysis of Randomized Trials of Antiplatelet Therapy for Prevention of Death, Myocardial Infarction, and Stroke in High Risk Patients", BMJ, 324:71-86.
Awtry et al. (2000) "Cardiovascular Drugs: Aspirin" Circulation, 101:1206-1218.
Bhatt et al. (2003) "Scientific and Therapeutic Advances in Antiplatelet Therapy" Nature Reviews, 2:15-28.
Campbell (1984) "General Properties and Applications of Monoclonal Antibodies" 1984 Elsevier Science Publisher, Section 1.1-1.3.4, pp. 1-29.
Chiabrando et al. (1987) "Antibody-Mediated Extraction/Negative-Ion Chemical Ionization Mass Spectrometric Measurement of Thromboxane B2 and 2,3-Dinor-thromboxane B2 in Human and Rat Urine" Analytical Biochemistry, 163:255-262.
Ellis et al. (1976) "Coronary Arterial Smooth Muscle Contraction by a Substance Released from Platelets: Evidence That It Is Thromboxane A2" Sceince 193:1135-1137.
Goding (1980) "Antibody Production by Hybridomas" Journal of Immunological Methods, 39:285-308.
Gum (2001) "Profile and Prevalence of Aspirin Resistance in Patients with Cardiovascular Disease" American Journal of Cardiology, 88:230-235.
Hamberg et al. (1975) "Thromboxanes: A New Group of Biologically Active Compounds Derived From Prostaglandin Endoperoxides" PNAS USA, 72(8):2994-2998.
Hankey et al. (2006) "Aspirin Resistance" Lancet, 367:606-617.
Hayashi et al. (1990) "Immunoaffinity Purification of 11-Dehydro-thromboxane B2 from Human Urine and Plasma for Quantitative Analysis by Radioimmunoassay" Analytical Biochemistry 187:151-159.
Helgason et al. (1994) "Development of Aspirin Resistance in Person With Previous Ischemic Stroke" Stroke, 25(12):2331-2336.
Hosoda et al. (1981) "Effect of Bridge Heterologous Combination on Sensitivity in Enzyme Immunoassay for Cortisol" Chem. Pharm. Bull., 29(7):1969-1974.
Lopez et al. (1998) "The Global Burden of Disease, 1990-2020" Nature Medicine, 4(11):1241-1243.
Sane et al. (2002) "Frequency of Aspirin Resistance in Patients With Congestive Heart Failure Treated with Antecedent Aspirin" The American Journal of Cardiology, 90:893-895.
Tarjan et al. (1999) Orv. Hetil, 140:2339-2343.
Tsuruta et al. (2003) "Characterization of 11-Dehydro-Thromboxane B2 Recombinant Antibody Obtained by Phage Display Technology" Prostaglandins, Leukotrienes and Essential Fatty Acids, 68:273-284.

* cited by examiner

*Primary Examiner* — Jacob Cheu
(74) *Attorney, Agent, or Firm* — Swanson & Bratschun, L.L.C.

(57) ABSTRACT

Methods, compositions and kits are provided for measuring aspirin's anti-thrombotic effectiveness on a subject. Included are a novel assay for quickly and specifically measuring TxA2 metabolite levels in urine and correlating the levels with aspirin dose in a subject. The methods, compositions and kits utilize a novel anti TxA2 metabolite antibody.

12 Claims, 12 Drawing Sheets

| Standard concentration | 11dhTxB2 | 11dh2,3DTxB2 |
|---|---|---|
| 1000 | 0.324 | 0.205 |
| 500 | 0.484 | 0.295 |
| 250 | 0.709 | 0.457 |
| 125 | 0.945 | 0.662 |
| 62.5 | 1.117 | 0.930 |
| 31.25 | 1.226 | 1.110 |
| (pg/ml) | (OD 405nm) | |

METHODS AND KITS FOR DETECTION OF THROMBOXANE A2 METABOLITES

RELATED APPLICATIONS

This application is a divisional of U.S. patent application Ser. No. 11/609,123 entitled "METHODS AND KITS FOR DETECTION OF THROMBOXANE A2 METABOLITES" filed Dec. 11, 2006, which claims priority under 35 U.S.C. 119(e) to U.S. Provisional Patent Application No. 60/748,788 entitled "METHODS, COMPOSITIONS AND ASSAYS FOR DETECTION OF THROMBOXANE A2 METABOLITES IN BIOLOGIC FLUID" filed Dec. 9, 2005, and to U.S. Provisional Patent Application No. 60/793,428 entitled "ANTIBODIES TO THROMBOXANE A2 METABOLITES, AND USES THEREOF" filed Apr. 19, 2006, the disclosures of which are hereby incorporated by reference in their entirety.

BACKGROUND OF THE INVENTION a. Field of the Invention

The invention generally relates to antibodies that bind two or more thromboxane A2 metabolites, and more particularly to antibodies that bind common epitopes in two or more target thromboxane B2 metabolites derived from thromboxane A2 and to the uses for these prepared antibodies.

b. Background

Aspirin (acetyl salicylic acid) has been in use in the United States for at least 100 years, with approximately 80 million aspirin tablets being consumed in America each day (self medicated or physician prescribed). Beyond pain relief, aspirin has been shown to reduce risk of cerebrovascular ischemia, myocardial infarction, angina, and recurrent blockage of arteries (collectively referred to as thrombotic disease (Antithrombotic Trialists' Collaboration, BMJ, 324:71-86, 2002)). Thrombotic disease is one of the world's leading causes of morbidity and mortality, and its prevalence is increasing (Lopez et al., Nat. Med., 4:1241-1243, 1998).

The Food and Drug Administration has recently recommended that persons suffering from thrombotic disease take from between 50 mg aspirin/day to 325 mg aspirin/day. However, higher doses of aspirin pose health risks in certain segments of the population, including stomach irritation, ringing in ears, allergic reactions and in children, Reye's syndrome.

Aspirin has been shown to inactivate cyclooxygenase (also known as COX or prostaglandin G/H synthase), a membrane bound enzyme responsible for the oxidation of arachidonic acid to prostaglandin $G_2$ (Awtry et al., Circulation, 101:1206-1218, 2000). This reaction is a precursor to the formation of a variety of prostanoids, including thromboxane A2 (TxA2), a potent platelet aggregator, and metabolites of thromboxane A2 such as thromboxane B2. In general, aspirin has been shown to reduce COX activity (there are actually two COX enzymes termed COX-I and COX-II) and thereby reduce the levels of downstream prostanoid development. Inactivation of these pathways ultimately limits thrombotic events by suppressing at least the ability of platelets to aggregate (Hamberg et al., PNAS, 72:2994-2998, 1975; Ellis et al., Science, 193:1135-1137, 1976).

Although the mechanism of aspirin inhibition of COX-1 is understood, recent studies suggest that not all users respond to aspirin to the same degree. A lack of response to aspirin in a user is generally referred to as "aspirin resistance." Person's suffering from aspirin resistance typically show either a lack of biochemical changes while on aspirin, i.e., user shows no or little reduction in TxA2 (and TxB2), platelet activation and/or aggregation, or the user may experience an ischemic event while on aspirin (Bhatt et al., Nature Rev., 2:15-28, 2003; Hankey et al., Lancet, 367:606-617). In either case, the prevalence of aspirin resistance in the population has been reported to be between 5 and 57% (Gum et al., Am J Cardiol, 88:230-235, 2001; Tarjan et al., Orv. Hetil, 140:2339-2343, 1999; Sane et al., Am J Cardiol, 90:893-895, 2002; Helgason et al., Stroke, 25:2331-2336, 1994). Identification of whether or not an individual is aspirin resistant prior to or during a thrombotic event would be extremely useful to a healthcare professional. An aspirin resistant individual would obviously receive an alternate dosage, drug or modified anticoagulant therapy.

Typically, studies using aspirin have focused on optimizing the amount of aspirin required for an individual to reduce the risk associated with thrombotic disease. Blood based assays have been developed that measure in vitro platelet aggregation as a measure of aspirin's effectiveness. However, these methods are not quantitative and can be affected by factors that are unrelated to aspirin sensitivity. In addition, a quantitative immunoassay is available for 11-dehydrothromboxane B2 (a TxA2 metabolite) detection in urine requiring the use of a polyclonal antibody to 11-dehydrothromboxane B2. The assay is helpful in that aspirin effectiveness can be determined from a subject's urine, but the polyclonal antibody does not provide highly reproducible or specific results.

U.S. Pat. No. 6,967,083 (herein '083) to Ens provides methods for identifying an optimal minimal aspirin dose for a patient that is specifically tailored to the patient's platelet response levels. The method utilizes a solid substrate coated by an agent capable of reacting with 11-dehydro thromboxane B2 in the urine, but provides little or no guidance as to how to reproducibly achieve this detection result given the tools described in the patent. For example, no agents in the '083 patent are described or shown that react with 11-dehydro thromboxane B2 or other thromboxane A2 metabolites.

As such, there is a need in the art to develop a highly specific and reproducible assay that measures effectiveness of aspirin in reducing platelet aggregation in a subject. The assay should be effective at measuring a dose of aspirin tailored to a particular subject for reducing thrombotic disease. In addition, there is a need in the art for a highly specific and reproducible assay that quickly identifies aspirin resistant individuals, thereby facilitating a health care professional's determination on a best course of treatment in the absence of aspirin.

Against this backdrop the present invention has been developed.

BRIEF SUMMARY OF THE INVENTION

The present invention provides methods for measuring the anti-thrombotic effectiveness of aspirin treatment on a subject. The methods also include identifying subjects that display aspirin resistance or tolerance. In some embodiments these methods take less than five hours and more typically less than three hours to complete. Embodiments of the invention typically include correlation between a subject's urine TxA2 metabolite level and the aspirin dose administered to the subject. In particular embodiments the invention includes correlation between a subject's urine 11dh TxB2 and 11-dehydro-2,3 dinor thromboxane B2 metabolite levels and the aspirin dose administered to the subject.

The present invention provides immunoassay-based kits for measuring TxA2 metabolite levels in urine. Kits provide assays that can be completed within five hours and more typically three hours. Kits also include a monoclonal antibody having reactivity with both 11 dh TxB2 and 11-dehydro-2,3 dinor thromboxane B2.

Finally, the present invention provides novel tools for identifying TxA2 metabolites in a biologic fluid, e.g., urine. In a preferred embodiment, novel tools are provided capable of identifying two or more TxA2 metabolites. In a particularly preferred embodiment, the tool comprises a monoclonal antibody derived from hybridoma number cells described herein. The monoclonal antibody having reactivity with two or more TxA2 metabolites and more particularly with the TxA2 metabolites: 11 dh TxB2 and 11-dehydro-2,3 dinor thromboxane B2.

These and various other features and advantages of the invention will be apparent from a reading of the following detailed description.

BRIEF DESCRIPTION OF THE DRAWINGS

Data within the following Figures is often expressed in terms of 11 dh TxB2, for purposes of the Figure legends and Figures, 11 dh TxB2 includes 11 dh TxB2 and 11-dehydro-2,3 dinor thromboxane B2.

DETAILED DESCRIPTION OF THE INVENTION

Figure 1:
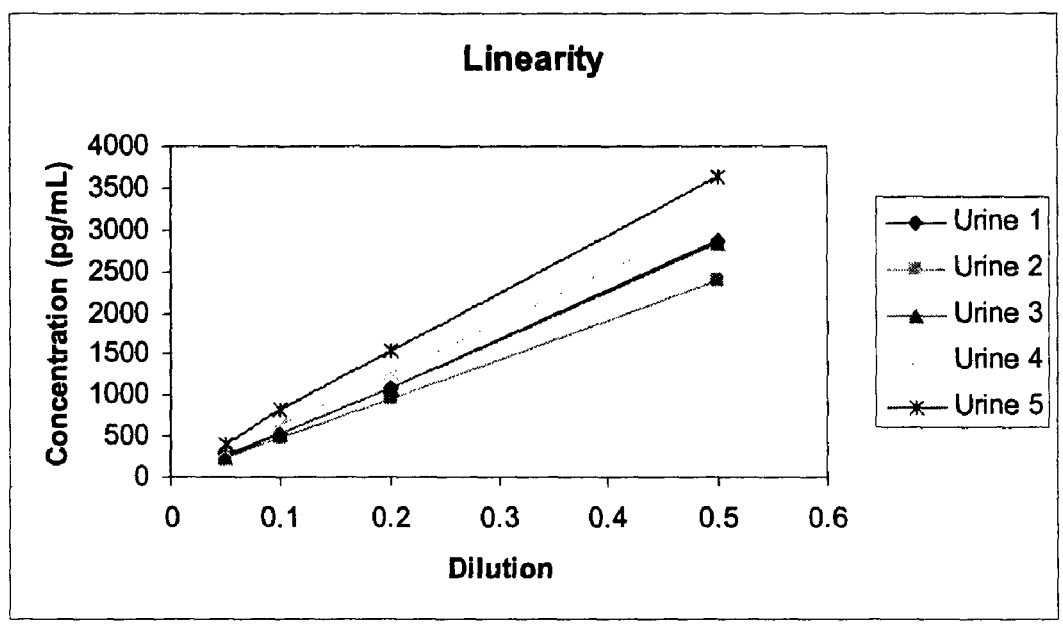
FIG. 1 is a linearity plot showing actual values of samples at various dilutions.

Aspects of the present invention include methods and assays for measuring the effectiveness of aspirin treatment in a subject, including methods and assays for identifying aspirin resistant subjects within a population. The methods and assays of the invention partly rely on improved immunoassays for highly sensitive, specific, timely and highly reproducible assays targeted at detection of one or more TxA2 metabolites in bodily fluids and especially in urine. Note that bodily fluids may also include blood plasma.

In one embodiment, the present invention provides a highly sensitive urine-based monoclonal ELISA for detection of 11 dhTxB2 and, in a preferred embodiment, at least one additional TxA2 metabolite. In a particularly preferred embodiment, the invention provides a highly sensitive urine-based monoclonal ELISA for detection of both 11 dhTxB2 and 11-dehydro-2,3 dinor thromboxane B2 (11 dh2,3dTxB2). As demonstrated herein, the detection of multiple TxA2 metabolites provides additional sensitivity and reproducibility as compared to assays that detect only one metabolite, i.e., 11 dhTxB2.

Anti 11 dhTB2 and 11 dh2,3dTxB2 Monoclonal Antibody

The present invention provides antibodies that specifically recognize two or more TxA2 metabolites and in particular recognize 11 dhTxB2 and 11 dh2,3dTxB2. As used herein the term antibody refers to proteins and fragments thereof, such as Fab, $F(ab)_2$, and Fv, where the fragments are capable of recognizing and binding either 11 dhTxB2 and/or 11 dh-2,3dTxB2.

The present invention provides monoclonal antibodies identified for their capacity to selectively bind the epitope presented by the structure shown in formula 1.

Formula 1:

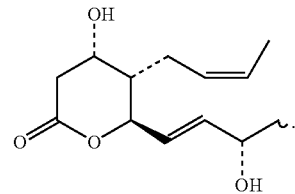

The specificity is defined by the fact that antibodies of the present invention react with 11 dh TxB2 and 11-dehydro-2,3 dinor thromboxane B2 but remain unreactive with 2,3 dinor TxB2, PGD2, TxB2,6-keto PGF1a, PGE2, PGEM or PGFM. (See, for example, Formulas 2-5 and Example 6).

Formulas 2-5, respectively:

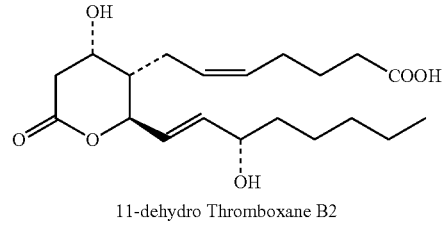

11-dehydro Thromboxane B2

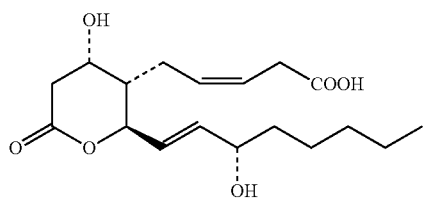

11-dehydro-2,3-dinor Thromboxane B2

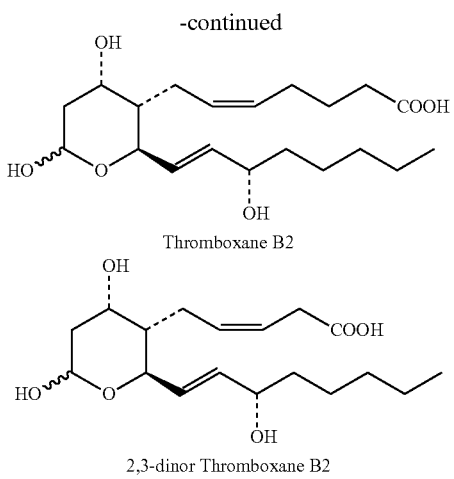

Thromboxane B2

2,3-dinor Thromboxane B2

In accordance with the present invention, monoclonal antibodies are selectively produced by immunizing an animal, e.g., mouse, rat, human, rabbit, horse, goat, etc., with an antigen having an epitope in common with 11 dh TxB2 and 11-dehydro-2,3 dinor thromboxane B2 (see, for example, Formula 1). The method includes immunizing an animal; selecting cells from the immunized animal that has been activated to express antibodies against two or more TxA2 metabolites, such as an epitope in common with 11 dh TxB2 and 11-dehydro-2,3 dinor thromboxane B2; fusing the harvested cells to myeloma cells e.g., SP 210, NS10, (or other like cells) to form hybridoma cells; selecting the hybridoma cells that secrete antibodies reactive to the appropriate antigen; and characterizing the antibody against the epitope in Formula 1.

The antibodies of the present invention can be isolated and purified by methods well known in the art, such as, for example, ammonium sulfate precipitation.

Various assays can be used to determine an antibody's immunogenic reactivity, such as competitive immunoprecipitation assays and the like.

Hybridoma cells that produce antibodies of the invention can be selected and isolated by various known methods in the art. In some embodiments, myeloma cells and lymphocytes activated against two or more TxA2 metabolites are cultured together in selection medium capable of killing the unfused myeloma cells but not the lymphocytes. Hybridoma cell lines of the invention form when myeloma cells fuse with lymphocytes capable of producing antibodies against two or more TxA2 metabolites. Fused cells are capable of survival in the selection medium while both unfused myeloma and lymphocytes are eliminated with time.

The potency or affinity that antibodies of the present invention have for two or more TxA2 metabolites is determined by enzyme-based competition assays (see Examples below) and by its utility in reacting with TxA2 metabolites in a subject's urine. For example, an antibody of the present invention shows at least 50% cross-reactivity with two or more TxA2 metabolites and preferably 50% cross-reactivity with 11 dh TxB2 and 11-dehydro-2,3 dinor thromboxane B2. In some embodiments, the cross-reactivity of the antibody is at least 50% with one of the TxA2 metabolites and at least 75% with an alternative TxA2 metabolite.

Embodiments of the present invention provide a significant improvement over previously developed polyclonal antibodies that recognize only 11 dhTxB2. As shown in Table 1 below, polyclonal antibodies against 11 dhTxB2 have proven to have suspect reproducibility toward binding of the 11 dhTxB2 epitope, especially as compared to the monoclonal antibodies of the present invention. In addition, whereas the polyclonal antibodies found in the prior art bind one TxA2 metabolite, 11 dhTxB2, the monoclonal antibodies of the present invention have been shown to reproducibly interact and bind at least two of the TxA2 metabolites, 11 dhTxB2 and 11 dh-2,3dTxB2. As such, the monoclonal antibodies of the present invention provide for enhanced specificity in diagnostic testing toward TxA2 metabolites and further for use in identifying aspirin resistant subjects.

In one embodiment, the antibodies of the present invention are obtained using the open form of 11 dhTxB2 as the immunogen or immunizing antigen. In some embodiments, especially due to its size, the 11 dhTxB2 is conjugated to a carrier protein, e.g., bovine serum albumin, goat serum albumin, etc. The coupled immunogen-carrier is then used to immunize a mouse or other like animal.

The production of the antibody can be performed by methods known in the art, for example, I. Lefkovits, Ed., (1996) Immunology Methods Manual Academic Press, Inc., San Diego, Calif. (incorporated herein by reference in its entirety). In typical embodiments the antibody is a monoclonal antibody. Hybridoma cell lines that produce the monoclonal antibodies of the present invention are typically produced by a fusion of an immortalized cell line with a B-lymphocyte and cells selected for antibody production that have affinity against 11 dhTxB2 and preferably both 11 dhTxB2 and 11 dh-2,3dTxB2. Clones were selected for sensitivity and selectivity toward both 11 dhTxB2 and 11 dh-2, 3dTxB2.

Hence embodiments of the invention include any monoclonal antibody that has affinity toward and binds to at least one TxA2 metabolite. In preferred embodiments, the invention includes any monoclonal antibody that has affinity toward and binds to more than one TxA2 metabolite, and in more preferred embodiments the TxA2 metabolites are 11 dhTxB2 and 11 dh-2,3dTxB2. In addition, embodiments of the present invention include cell lines that produce these antibodies, and in particular, hybridoma cell lines.

Urinary 11dhTxB2 Competitive ELISA Assay

An important part of antiplatelet therapy in cardiovascular disease is aspirin, known for its antiplatelet effects. Low dose aspirin blocks more than 95% of platelet COX-1 activity and reduces cardiovascular events by as much as 25% in patients with arterial vascular disease. Unfortunately, aspirin is not effective in all individuals. This phenomenon has been deemed aspirin resistance, and 5-57% of aspirin users fall within this category of not responding to the antiplatelet therapy of aspirin.

Measurements of stable metabolites to TxA2, such as 11 dhTxB2 and 11dh-2,3DTxB2, which are found in urine, provide an excellent measure of TxA2 production by platelets and thus an improved tool for analyzing aspirin's effectiveness.

Figure 6A:
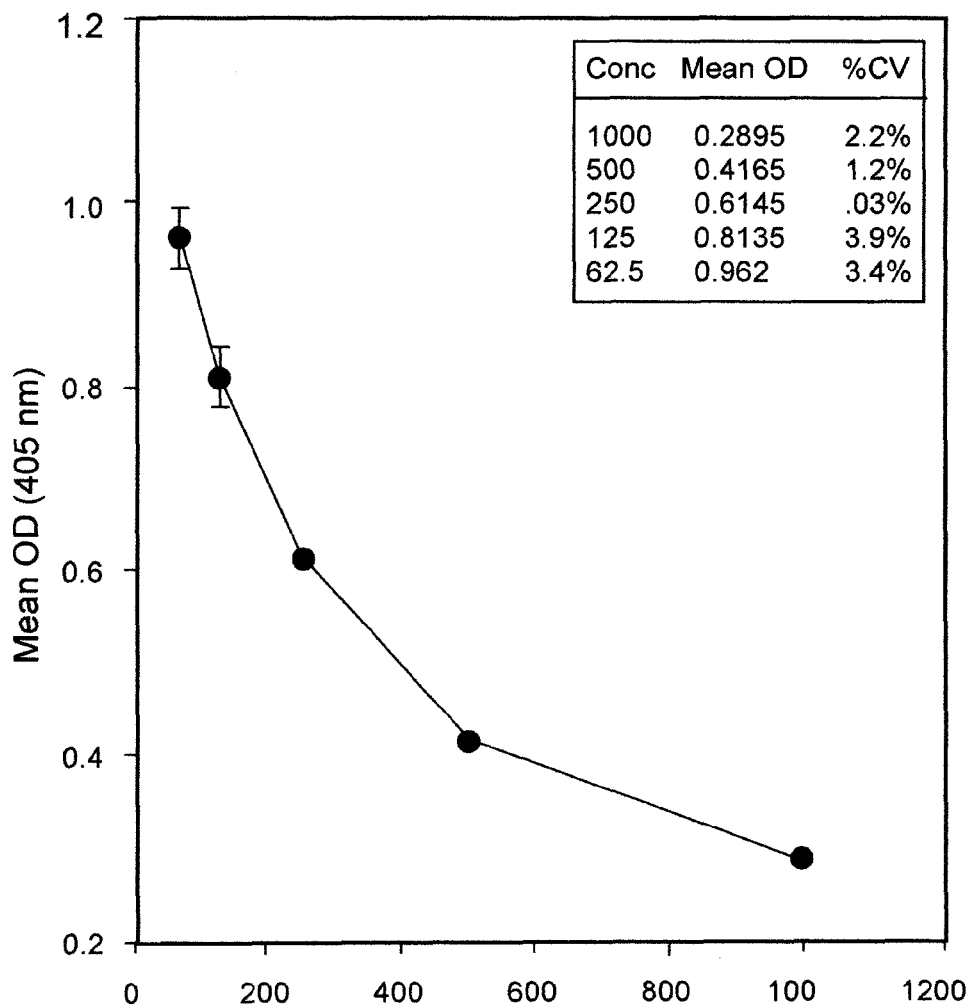
FIG. 6a is a standard curve of OD readings at 405 nm for varied 1 ldhTxB2 concentrations (between 100 pg/mL and 1,000 pg/mL)
Figure 6B:
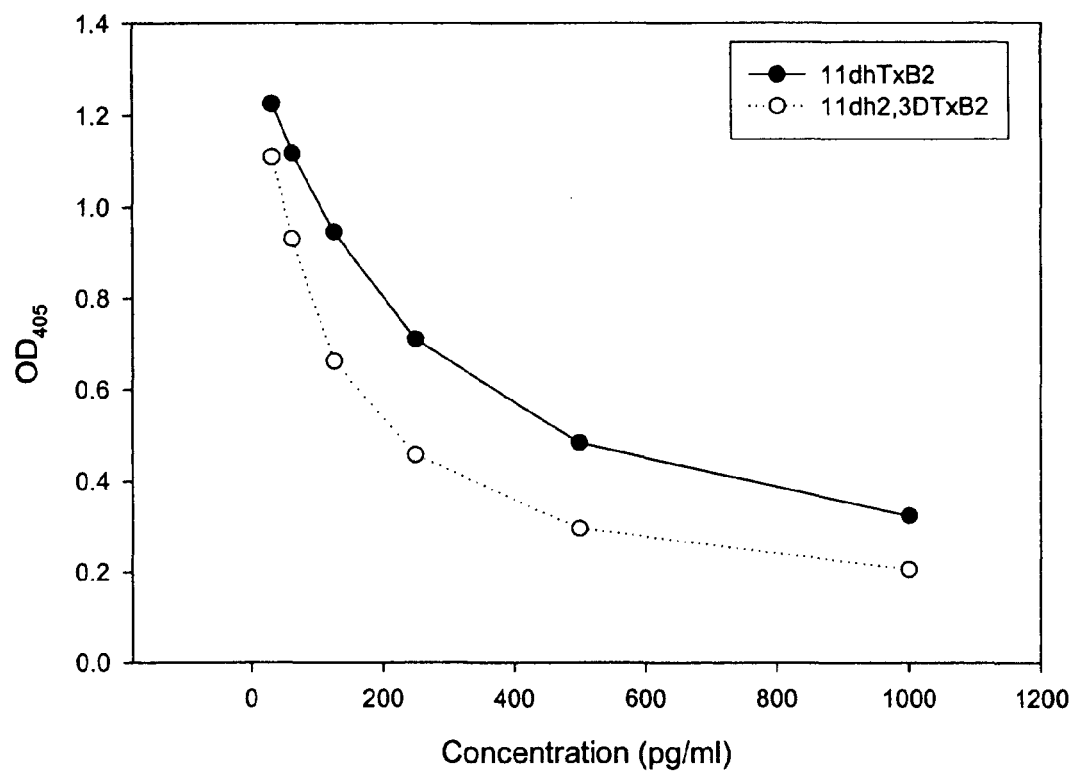
FIG. 6b is a standard curve of OD readings at 405 nm for varied 11dhTxB2 and 11-dehydro-2,3 dinor thromboxane B2.

The present invention provides a urinary 11dhTxB2 Competitive ELISA Assay. An illustrative standard curve was prepared (see FIG. 6) by spiking known amounts of 11dhTxB2 into low level urine diluted 1:5 in Tris assay buffer (0.1M Tris, 0.1% BSA) or into assay buffer alone. 100 μl of standards or actual samples (having taken known amounts of aspirin and diluted 1:5 in Tris assay buffer) was added to wells coated with goat anti-mouse antibody, followed by the addition of 50 μl of 11 dhTxB2-AP (alkaline phosphatase) tracer and 50 μl of 11 dhTxB2 mAb. The reactions were then allowed to incubate for a predetermined amount of time, typically with shaking at room temperature. In preferred embodiments the incubation is about two hours in length. Each well is then washed with a wash buffer and approximately 200 μl of substrate added (p-nitrophenyl-phosphate, pNPP). The reactions are then incubated again for approximately thirty minutes. A stop solution is added to each well, and the plate read for OD at 405 nm.

Results from the assay provide for the amount of 11dhTxB2 and 11 dh-2,3dTxB2 present in the sample (note that results are compared to the standard curve). The amount of the two metabolites present in the sample is indirectly proportional to the optical density read at 405 nm. For clinical samples, creatinine values are also obtained, and data from assays presented as pg metabolite/mg creatinine.

In some cases where the assay reliability is known or where the accuracy of the assay is not critical, a standard curve can be avoided.

Polyclonal Antibody (Prior Art) vs Monoclonal Antibody of the Invention

A monoclonal-based assay of the invention was compared to a standard polyclonal assay using twelve urine controls, run multiple times over a period of six months. The controls were derived from aspirin users as well as non-users. The % CV (coefficient of variance) range in the monoclonal assay was 0.3%-12.9% with an average of 3.7% (see Table 1). The % CV range in the polyclonal assay was 0-35.8% with an average of 9.9%. In comparing standard curves, the $R^2$ (coefficient of regression) value of the monoclonal assay averaged 0.9973 compared to 0.9877 for the polyclonal assay. To further compare the mAb and pAb assays, an additional urine panel was established consisting of ten samples from both aspirin users and non-aspirin users, and metabolites from the two assays compared. The correlation (r) between the methods was 0.944, confirming the clinical relevance of the monoclonal-based assay of the invention. Thus, this sensitive, urine-based monoclonal ELISA for TxA2 metabolites detection eliminates the potential for analytical variables that can occur in other assays.

Note that precision data collected on four different samples (n=69) showed good intra-assay precision (average of 1.7%) as well as good inter-assay precision (also 1.7%).

TABLE 1

Monoclonal Antibody and Polyclonal Antibody Comparison

| | Polyclonal Antibody | | Antibody of the Invention | |
|---|---|---|---|---|
| Sample No. | Mean (pg/mL) | % CV | Mean (pg/mL) | % CV |
| 1 | 184 | 14.0 | 504 | 4.4 |
| 2 | 210 | 7.5 | 756 | 3.5 |
| 3 | 323 | 8.9 | 1069 | 5.2 |
| 4 | 158 | 12.6 | 493 | 5.2 |
| 5 | 279 | 6.1 | 1136 | 2.1 |
| 6 | 822 | 15.6 | 3303 | 2.4 |
| 7 | 166 | 11.6 | 453 | 2.8 |
| 8 | 272 | 12.2 | 1176 | 3.4 |
| 9 | 794 | 6.7 | 2860 | 5.3 |
| 10 | 188 | 9.5 | 439 | 6.1 |
| 11 | 305 | 6.6 | 1115 | 2.0 |
| 12 | 762 | 7.5 | 3088 | 2.3 |
| Mean % CV | | 9.9 | | 3.7 |

Data shown in Table 1 provide strong evidence that the mAb based ELISA, recognizing two TxA2 metabolites, provides a significant improvement (reproducibility and specificity) in measurement of TxA2 metabolites as compared to polyclonal based detection systems. As such, the assays of the present invention provide a significant benefit in clinical use when analyzing aspirin effectiveness on subjects.

The following examples are offered to further illustrate the invention and are not meant to limit the invention in any manner.

EXAMPLES

Example 1

Preparation of 11-Dehydro Thromboxane-Hapten Carrier Immunogen 11-dehydro Thromboxane B2 was purchased from Cayman Chemical, Catalog Number 419504. The identity of the compound can be verified by mass spectroscopy (Finnegan ICQ, negative ion mode) and by HPLC. The compound was purified to greater than 98% purity using normal phase silicic acid chromatography. Three milligrams of the purified compound was then suspended in 100 μl of absolute ethanol. The ethanolic solution of 11-dehydro Thromboxane B2 was then added to 500 μl of 0.1M potassium phosphate buffer, pH of 7.4, and 5 mg Keyhole Limpet Hemocyanin (Cape Cod Associates), vortexed, and transferred to a 5 ml V-bottom vial equipped with a magnetic stirrer and charged with 5 mg of solid EDC. The V-bottom vial was wrapped in aluminum foil and placed on a magnetic stir plate at ambient temperature (~22° C.) overnight. The contents of the vial were then dialyzed through a 10,000 MW cut-off membrane for 8 hours against 7.4 liters of 0.1M potassium phosphate buffer, pH 7.4. The volume was standardized to 5 ml with distilled water and 100 μl aliquots were frozen at −20° C. for immunization (aliquots termed immunogen herein).

Example 2

Preparation of Tracers Used in Antibody Screening

Anhydrous dimethyl formamide (DMF) was prepared by distillation and storage over molecular sieves. Dry DMF was used to prepare 10 mM solutions of N-hydroxy succinimide, dicyclohexyldicarbodiimide, and 11-dehydro Thromboxane B2. Each compound was prepared in a 10 ml reactivial that was oven dried and stored in a desiccator. In a new, dry 5 ml V-bottom reactivial, 10 μl of each solution was passed, vortexed briefly, sealed with a septum cap and allowed to incubate at ambient temperature overnight. The next day, 250 μl of 0.1M borate buffer, pH 8.5, was added, along with 2,000 Units of alkaline phosphatase. The resulting mixture was incubated in the dark for approximately 30 minutes at ambient temperature, then purified over a 30×2 Sephadex G-25 medium column. Fractions were eluted using 0.1M Tris buffer, pH 7.4. One milliliter fractions were collected and pooled based on the fractions in which activity to p-nitrophenyl phosphate was detected. The tracer was diluted to a specific activity of 0.5 AU/μl/s, and 50 μl of tracer solution was used to screen specific antibody in 96-well microplates coated with goat anti-mouse IgG.

Example 3

Immunization of BALB/C Mice

Four to six week-old BALB/C mice (purchased from Charles River) were injected into the peritoneum with equal volumes of immunogen (~100 μg) and Freunds complete adjuvant. A second substantially identical immunization was given each mouse 14 days later and a blood test obtained on day 24, i.e., blood test given to each mouse 10 days after the second immunization. A number of mice showed good antibody binding response to 11-dehydro Thromboxane B2 tracer. Mice showing a high titer of serum antibody to 11-dehydro Thromboxane B2 were given a boost of 100 µg immunogen in complete Freunds adjuvant and a second test bleed was taken on day 44. Those mice with continued high titers were given a second booster injection of immunogen in incomplete Freunds adjuvant. Five days after the second boost, target mice were ready for removal of spleen.

Example 4

Preparation, Characterization and Purification of Hybridoma Antibodies

A fusion reagent was prepared by first weighing out 4.2 g of polyethylene glycol (PEG) 4000. The PEG was then liquefied by autoclaving. While the PEG is still liquefied, 1.5 ml of DMSO (q.s. to 10 ml with DPBS and $CaCl_2$ (anhydrous) (50 mg/500 ml) and $MgCl_2$ (hexahydrate (50 mg/500 ml)) is added. The solution can be stored at 4° C.

To prepare for the fusion procedure, the fusion reagent (42% PEG 4000+15% DMSO in DPBS with Ca and Mg) is warmed to 37° C. Approximately 50 ml sterile RPMI 1640 is added to a 50 ml conical tube and placed at 4° C.

Approximately 60 ml of HAT selection medium (20% HI FBS+1×HAT+1×L-glutamine+1× pen/strep+10% NCTC-109 medium+3 ml hybridoma cloning factor (IL-6 secreted from cell line which is purchased from Fisher)) is added to RPMI 1640. The HAT selection medium is filtered through a 0.2 µm filter unit.

Myeloma cells (SP2/0 cells) were prepared by obtaining 18-20×$10^6$ cells which were spun down at 1000 rpm for 7 to 8 minutes. The supernatant was aspirated and the cell pellet re-suspended in 10 ml cold RPMI 1640. The cells were washed a second time and re-suspended in 5 ml cold RPMI 1640. Myeloma cells were recounted to ensure cell numbers.

Target mice were euthanitized using $CO_2$. The left side of the mouse was sprayed with 70% ethanol and the spleen removed using sterile scissors and forceps. The removed spleen was placed into a sterile P60 dish with approximately 5 ml RPMI 1640. The spleen was rinsed and transferred into a second sterile P60 dish. The spleen was perfused and then minced with sterile forceps to remove the connective tissue. The minced spleen was then transferred into a sterile 15 ml conical tube and the clumps of tissue allowed to settle to the bottom of the tube for two minutes. The cells were then agitated using a pipet and transferred (without the clumps) to a new 15 ml conical tube. The cells were spun down at 1000 rpm for 7 to 8 minutes. Supernatant was removed and the cells re-suspended in 3 ml of cold RPMI 1640. One milliliter of the splenocyte suspension was transferred into a second 15 ml sterile conical tube. The cells were pelleted as above and approximately one milliliter of heat inactivated FBS with 5% DMSO was added to the cells and the combination frozen. These cells were saved in case the fusion procedure failed.

Eight milliliters of cold RPMI 1640 was added to the 2 ml of remaining splenocytes. The cells were then spun down at 1000 rpm for 7 to 8 minutes. The pelleted cells were re-suspended in 5 ml of cold RPMI 1640 and counted (use multiple dilutions).

With regard to the fusion, a 4:1 ratio of splenocytes:myeloma cells was combined into a 50 ml conical tube. The combined cells were pelleted at 1000 rpm for 7 to 8 minutes and the supernatant aspirated. The cell pellet was loosened by agitating the tube with a finger. Over the course of one minute, 1.5 ml of fusion reagent was added to the pellet and the mixture agitated for 20 to 30 seconds. Over the course of the next minute, 10 ml of warm RPMI 1640 was added to the cells. The cells were then spun at 1000 rpm for 7 to 8 minutes. The supernatant was removed from the cell pellet and the cells re-suspended in 50 ml of HAT selection medium. Cells were plated into 8 plates and allowed to incubate in a 37° C. incubator (5% $CO_2$) for 4 to 5 days.

Unfused cells were found dead after the 4 to 5 day period. New medium was combined into the plates including additional HAT selection medium. The cells were allowed to grow for 10 to 14 days.

Example 5

Hybridoma Screening Assay

Fusion cell supernatants were screened using a goat anti-mouse coated plate purchased from Cayman Chemical (Catalog number 400009). Approximately 100 µl of supernatant from each plate was added to the Cayman plate along with 100 µl of 11-dehydro Thromboxane B2-Acetylcholinesterase tracer (see above). Note that appropriate positive and negative controls were run on the Cayman plate, i.e., 100 µl HAT selection medium, 100 diluted mouse serum. Reactions were allowed to incubate overnight at ambient temperature. Plates were washed with appropriate wash buffer and 300 µl/well of Ellman's reagent buffer (substrate) added. Those cells corresponding to supernatant that had a strong absorbance at 415 nm were expanded.

In particular, cells from individual well that tested positive were expanded into E-well plates in HAT medium. Once cell growth in these vessels provided sufficient testing material, supernatants were re-screened to eliminate false positives and to eliminate clones that stopped producing appropriate antibody. Positive clones were expended into T25 flasks to provide sufficient material to further characterize antibodies of the present invention.

Example 6

Preparation of a Monoclonal Antibody that Recognizes Two or More Thromboxane A2 Metabolites Two forms of 11dhTxB2 are in an equilibrium (open and closed). As analyzed by HPLC, the compound in ethanol was found to be predominantly in a closed form (93%), the remaining 7% being in an open form. After evaporation of the solvent, the carboxyl group of 11dhTxB2 (200 µg) was coupled to an amino group of bovine serum albumin (2 mg) by the N-succinimidyl ester method in the presence of phosphate buffer, pH 7.4. (Hosoda, H, et al., Chem. Pharm. Bull. 29:1969-1974, 1981). The conjugate thus prepared was stored in the same buffer. Three female BALB/c mice 6 weeks of age were first immunized by intraperitoneal injection of the conjugate (5.5 µg of 11dhTxB2, 80 µl of protein), which was emulsified with an equal volume of complete Freund's adjuvant. Two more injections were given every 2 weeks in the same way except that incomplete Freund's adjuvant was used. The last immunogen was given in 0.2 ml of saline without adjuvant. The antibody was titrated using 11-[$^3$H] dhTxB2 methyl ester, which was dissolved in phosphate buffer (pH 7.4) and therefore in an open form. Three days after the last antigen injection, the spleen was removed from a mouse with the highest titer of antibody. Fusion of the spleen cells with an aminopterin-sensitive myeloma cell line (SP2/0-Ag14) was performed using 50% polyethylene glycol-1000 by the method of Goding (Goding, J. W., J. Immunol. Methods 39:285-308, 1980). After a 12-day incubation in 96-well culture plates, the medium containing hypoxanthine, aminopterin, and thymidine was replaced by a medium containing hypoxanthine and thymidine in which Ultroser G substituted for serum. After a 2-day culture in this serum-free condition, an aliquot of the medium was removed for titration of antibody by radioimmunoassay using 11-[$^3$H]dhTxB2 methyl ester. Selected hybridoma cells were cloned twice in soft agar according to the method of Kennet (Kennet, R. H., in Monoclonal Antibodies (Kennet, R. H. and McKearn, T. J., Eds.), pp. 372-373, 1980). A clone producing anti-11dhTxB2 antibody was injected into the peritoneal cavity of BALB/c mice previously treated with pristine. The antibody in the ascites fluid was collected with ammonium sulfate at 50% saturation, and was further purified by the use of a protein A-Sepharose column (Oi, V. T. and Herzenberg, L. A., in Selected Methods in Cellular Immunology (Mishell, B. B. and Shiigi, S. M., Eds.), pp. 351-372, 1980). About 20 mg of IgG were obtained from one mouse (Hayashi Y., et al., Anal. Biochem. 187: 151-159, 1990).

Example 7

Monoclonal Antibody Specificity

Antibody clones of the invention were tested to determine cross-reactivity against various Thromboxane A2 metabolites and other like compounds. Table 2 provides percent cross reactivity of antibodies of the present invention against these various compounds:

TABLE 2

Cross Reactivity

| Compound | % Reactivity |
| --- | --- |
| 11 dh TxB2 | 100% |
| 11-dehydro-2,3 dinor thromboxane B2 | 166% |
| 2,3 dinor TxB2 | 1.93% |
| PGD2 | 0.2% |
| TxB2 | 0.05% |
| 6-keto PGF1a | <0.01% |
| PGE2 | <0.01% |
| 2,3,4,5-tetranor-20-Carboxy 13,14-dihydro-15-keto PGE2 (PGEM) | <0.01% |
| 2,3,4,5-tetranor-20-Carboxy 13,14-dihydro-15-keto PGF2α (PGFM) | <0.01% |

Data in Example 7 shows the high reactivity of monoclonal antibodies of the present invention toward 11 dh TxB2 and 11-dehydro-2,3 dinor thromboxane B2. Specificity is illustrated by the antibodies failure to react with the other enumerated compounds.

Example 8

Kits of the Invention Show a High Level of Precision

Kits of the invention were tested for precision between three different plates/kit lots. Three urine samples were chosen of low, moderate, and high TxA2 metabolite values (L, M, and H). Each sample was run on 24 wells/plate over three plates from three separate kit production lots. Values were obtained and the mean, standard deviation, and % coefficients of variation (% CV) were calculated and shown for each sample for inter- and intra-assay precision.

TABLE 3

Precision Testing

| Sample No. | Mean | Std Dev. | Inter-Assay Precision | Mean Intra-Assay Precision |
| --- | --- | --- | --- | --- |
| H | 3380 | 334 | 9.9% | 5.7% |
| M | 1399 | 116 | 8.3% | 6.7% |
| L | 424 | 63 | 14.9% | 10.3% |

Example 9

Kits of the Invention are Highly Accurate and Sensitive

Linearity of the kits of the present invention were monitored by measurement of TxA2 metabolites in the urine of subjects, where the urine was diluted to three different dilutions. Five different samples (Urine 1-5) at four different dilutions each (1:2, 1:5, 1:10 and 1:20) were run using the kits of the invention. Values are shown in Table 4. Dilution factor, mean, standard deviation, and % CV are shown for each sample. The data illustrates the utility of the kits of the invention.

TABLE 4

Linearity of Kits of the Invention

| Dilution | Urine 1 | Urine 2 | Urine 3 | Urine 4 | Urine 5 |
| --- | --- | --- | --- | --- | --- |
| 1:2 (0.5) | 2867 | 2395 | 2837 | 3115 | 3640 |
| 1:5 (0.2) | 2734 | 2377 | 2717 | 3190 | 3824 |
| 1:10 (0.1) | 2670 | 2340 | 2708 | 3187 | 4049 |
| 1:20 (0.05) | 2618 | 2372 | 2509 | 3105 | 3912 |
| Mean | 2722 | 2371 | 2693 | 3149 | 3856 |
| SD | 108 | 23 | 136 | 46 | 171 |
| % CV | 4.0% | 1.0% | 5.0% | 1.4% | 4.4% |

The data in Table 4 was plotted on a linearity plot as shown in FIG. 1. The data in Table 4 and FIG. 1 show the excellent sensitivity and accuracy of the kits of the present invention.

Figure 2:
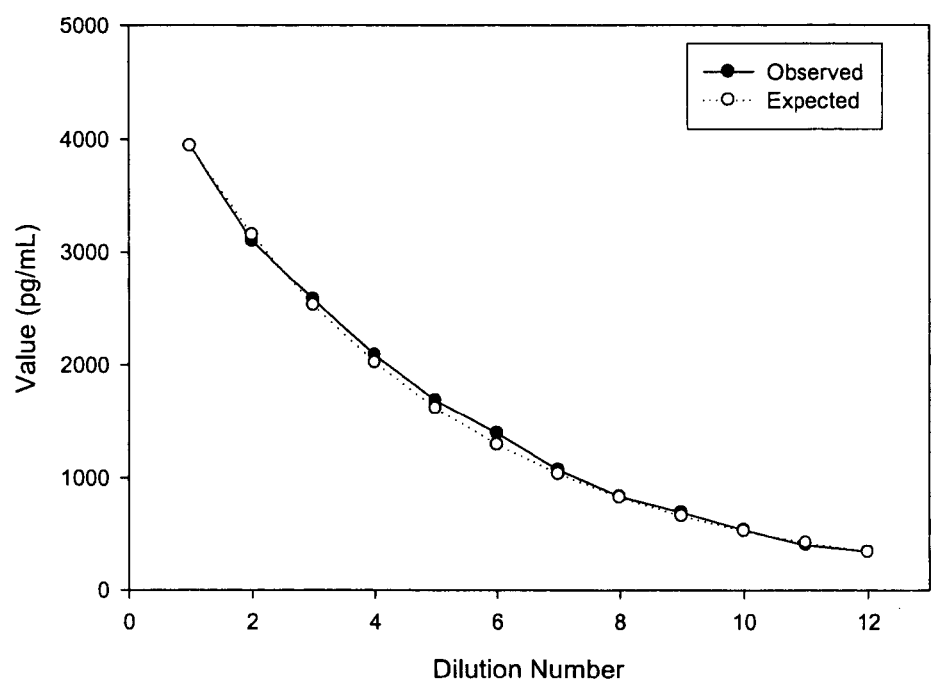
FIG. 2 is a recovery assay plot showing the excellent correlation between observed and expected values when testing samples using embodiments of the present invention.

A recovery assay plot was performed using kits of the invention. A urine sample containing a high value of TxA2 metabolites was serially diluted 1:1.25 and run on a kit of the invention. A value was obtained for Dilution #1, and the expected concentrations of each dilution calculated based on a 1.25-fold dilution of the observed value of Dilution #1. The observed values were compared to the expected value and are shown in FIG. 2. The data of FIG. 2 illustrates the highly accurate and sensitive nature of the kits and methods of the invention.

Figure 3:
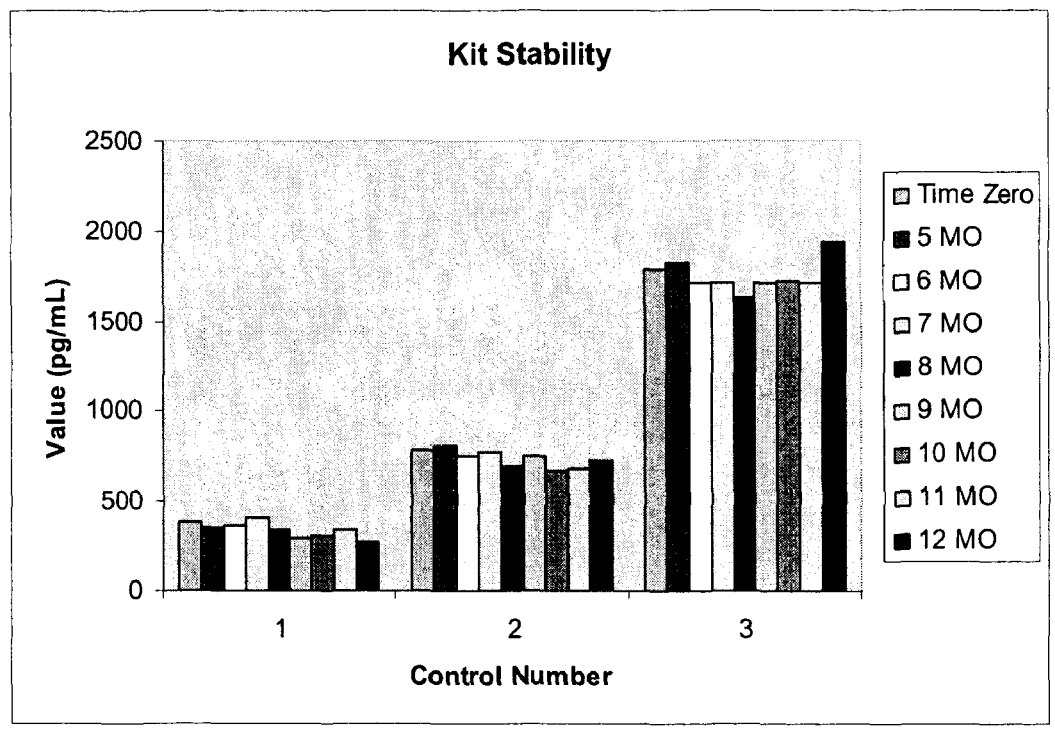
FIG. 3 is a bar graph showing the high kit stability of embodiments of the present invention.

It was further determined that kits of the invention are highly stable over long periods of time. As shown in FIG. 3, three control samples were tested using the kits of the invention, each sample being tested over a 12 month period. The data in FIG. 3 shows that the methods and kits of the invention are useful for testing samples over an extended period of time.

Example 10

Clinical Findings for 1,500 pg TxA2 Metabolites/mg Creatinine Threshold

Initially, 171 urine samples were taken from subjects either off aspirin or on 81 or 325 mg aspirin/day. TxA2 metabolite amounts were determined for each sample using the methods and kits of the present invention. Values were normalized for urinary dilution by dividing TxA2 metabolite amounts by creatinine concentrations.

Figure 4:
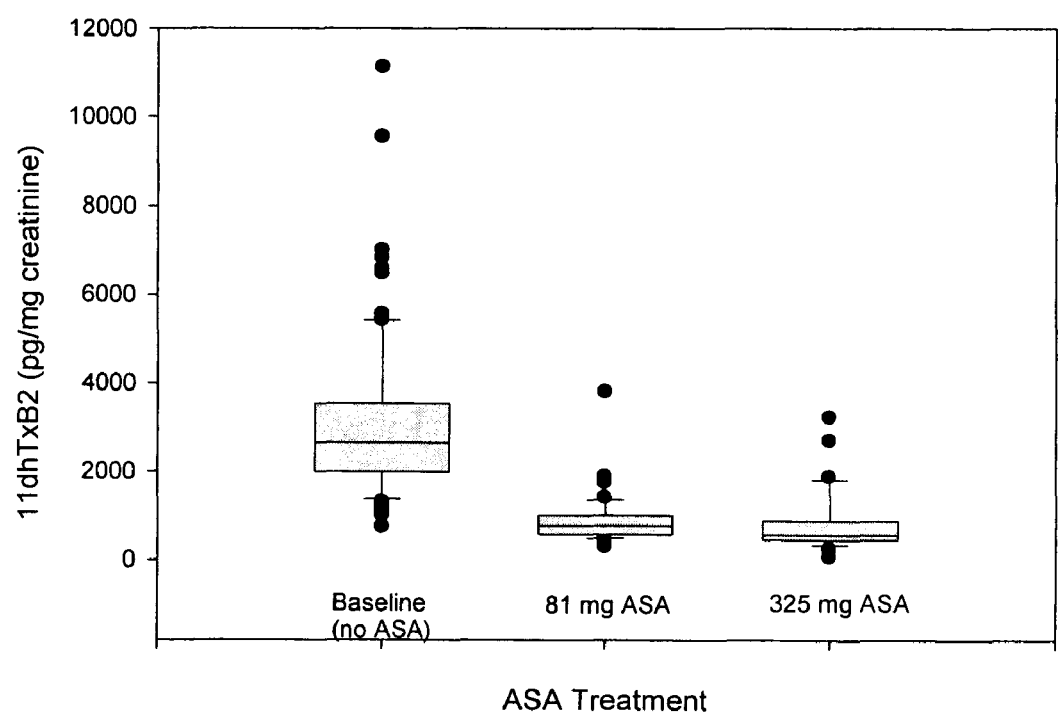
FIG. 4 is a box plot comparison of 11 dh TxB2 against samples from aspirin users.

FIG. 4 shows a box plot comparison of 11 dh TxB2 baseline levels (representing all TxA2 metabolite amounts) against each category of aspirin user (none, 81 mg or 325 mg). Boxes in FIG. 4 represent 75/25 percentiles and the horizontal line within the box represents the median for each group. Dots are samples outside the 90/10 percentile bars.

354 urine samples from subjects either on or off aspirin therapy were run using the methods and kits of the present invention. Values were calculated and normalized for urinary dilution by dividing by creatinine concentration, and the frequency of each concentration was calculated and shown in a frequency plot, FIG. 5. Subjects on aspirin are plotted with solid bars and subjects not on aspirin are plotted using hatched bars.

Aspirin response data was then plotted for the 354 samples graphically, as shown in Table 5. Positive samples are below 1500 pg/mg creatinine cutoff, whereas negative samples are those that are above the 1500 pg/mg creatinine cutoff.

The data shows the utility of using a 1500 pg TxA2 metabolite/mg creatinine cutoff.

TABLE 5

| | Clinical Response | |
|---|---|---|
| | Aspirin Ingestion | |
| Results | Present | Absent |
| Positive (<1500 pg/creatinine) | 251 | 9 |
| Negative (>1500 pg/creatinine) | 16 | 78 |

Example 11

Clinical Findings Using a Urinary TxA2 Metabolite Based Competitive ELISA Assay

Figure 5:
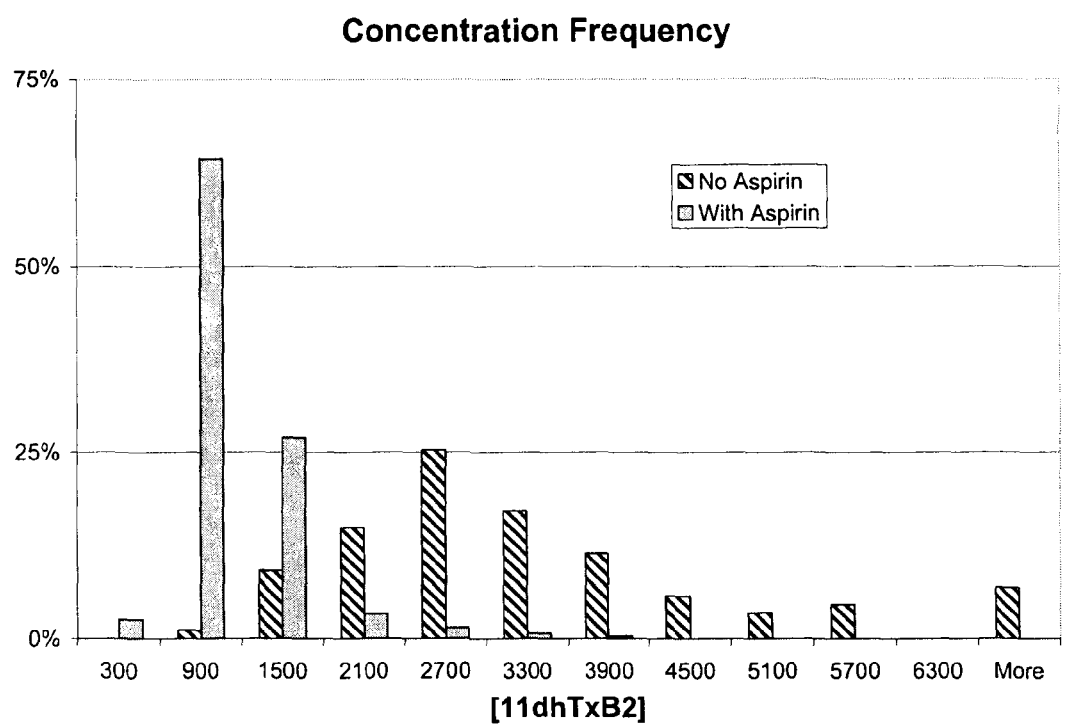
FIG. 5 is a frequency plot of urinary 11 dh TxB2 values from subjects on aspirin or subjects not on aspirin.

As shown in FIGS. 4-5, clinical data can be obtained using the above-described methods. Standard curves (FIG. 6) showed good reproducibility, with % CV in the range of 0.3-3.9% (6a) and detects both 11 dh TxB2 and 11-dehydro-2,3 dinor thromboxane B2 (see FIG. 6b). The assay detection range was suitable for measurement of 11dhTxB2 in a population (62-3122 pg 11dhTxB2/mg creatinine—see FIG. 7). The healthy samples in the study were normally distributed with an average value of 1119 pg/mg, and aspirin use resulted in decreased patient values (81, 162 and 325 mg/day values at 418, 471 and 377 pg/mg, respectively) (see FIG. 8 and FIG. 9). All three levels of aspirin doses are statistically significant when compared to the healthy, no aspirin controls.

Note that there was more variability in the 81 mg and 162 mg samples than in the 325 mg samples, as these dosages may not be optimal for some patients in reducing 11dhTxB2 levels. There were samples in the aspirin treated groups with high levels of 11dhTxB2, which may represent aspirin-resistant individuals.

Figure 7:
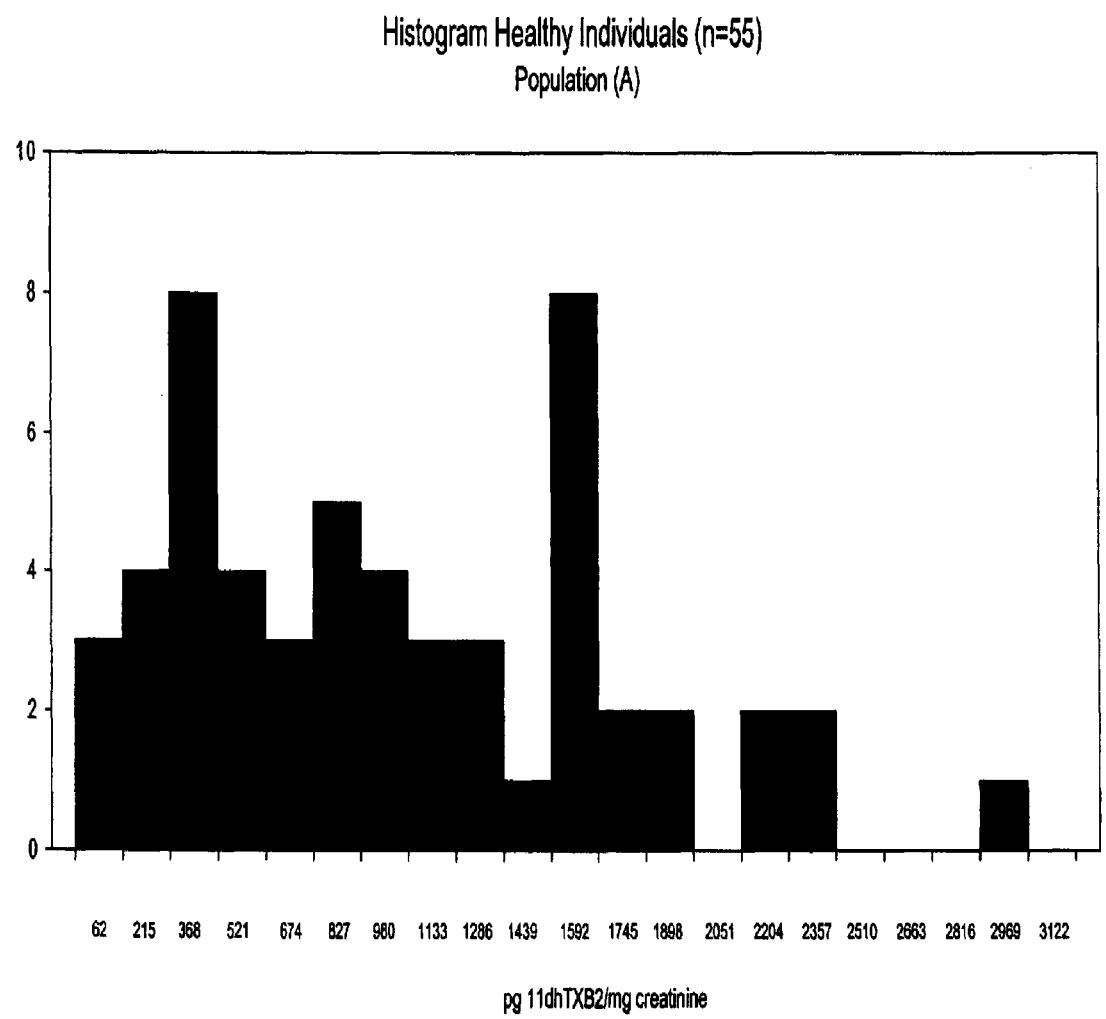
FIG. 7 is a histogram representing 11dhTxB2 levels in 55 normal individuals, the 11dhTxB2 determined in accordance with embodiments of the present invention.
Figure 8:
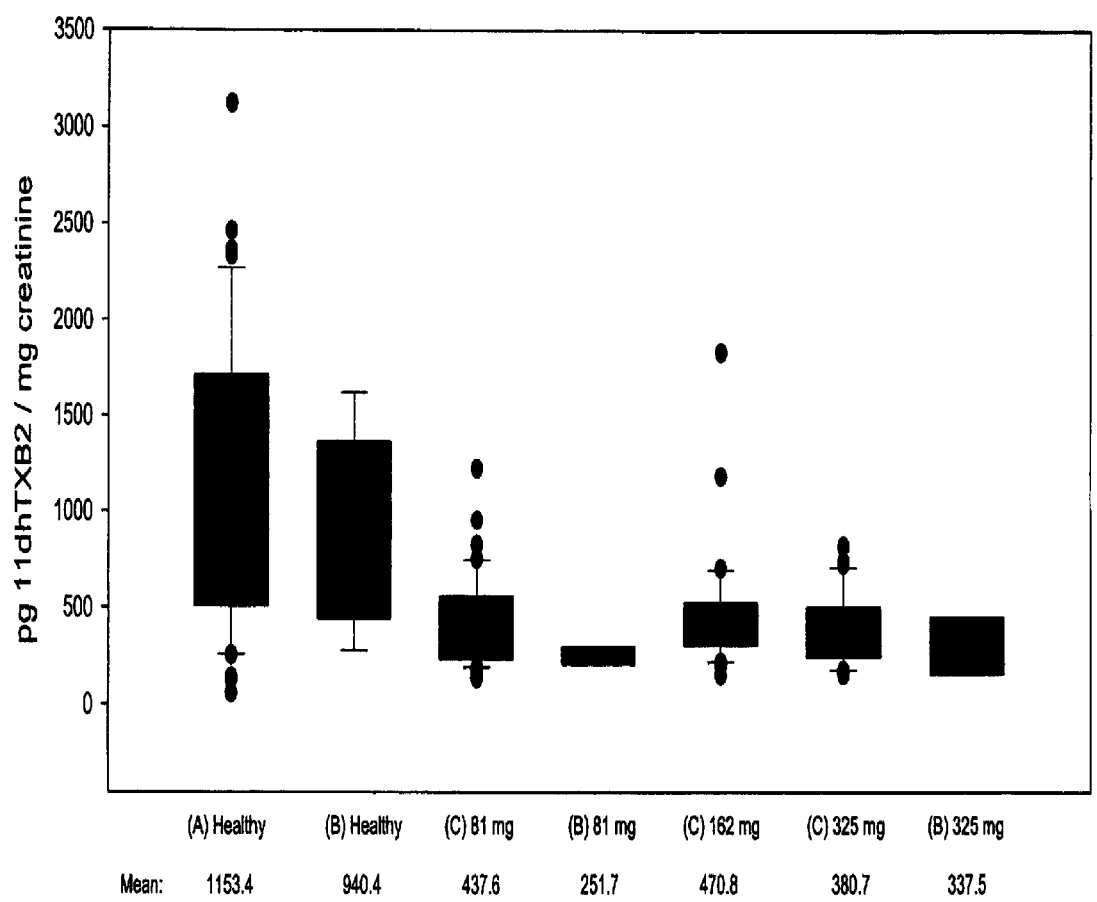
FIG. 8 shows a comparison of 11dhTxB2 levels in normal individuals (no aspirin) and individuals treated with either 81 mg, 162 mg or 325 mg aspirin.
Figure 9:
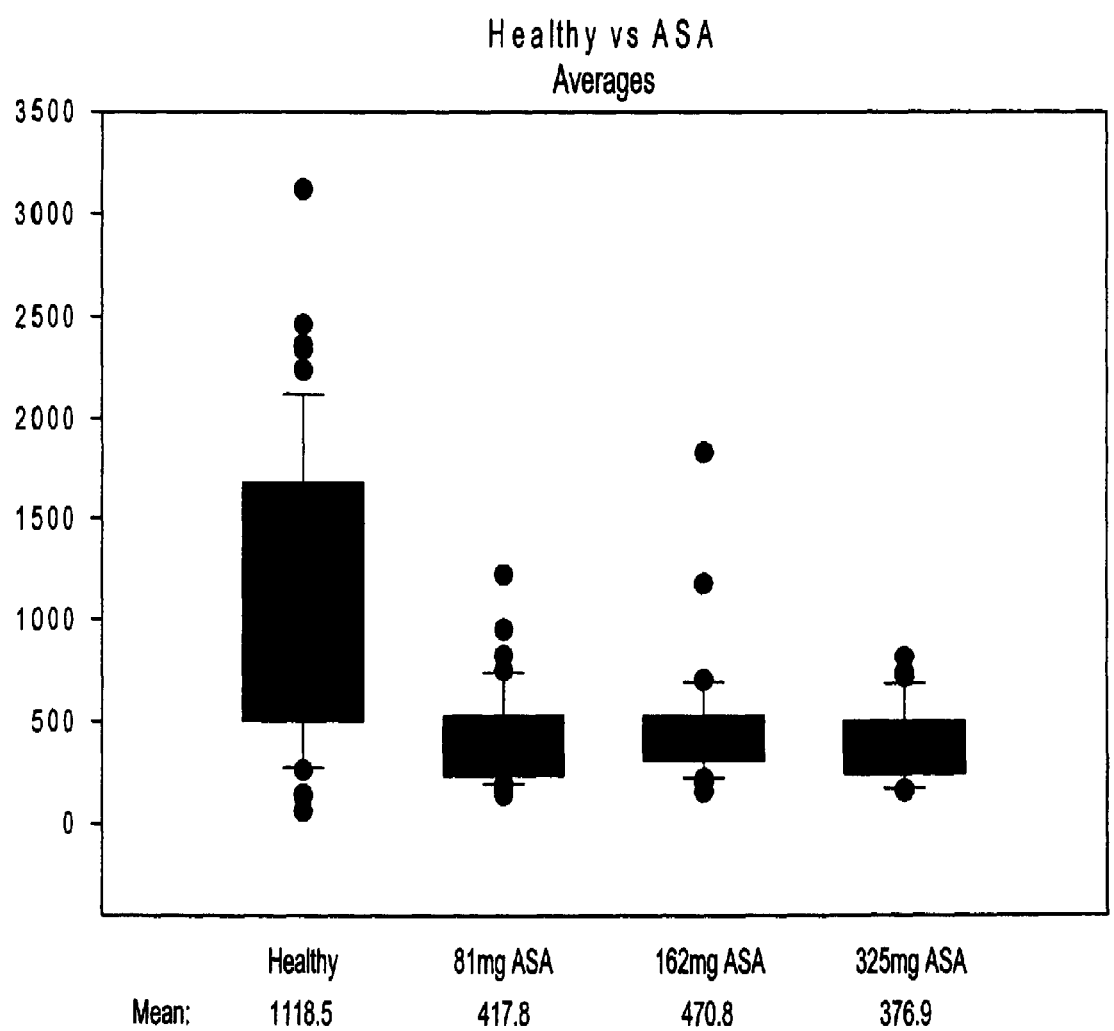
FIG. 9 shows average 11dhTxB2 levels in normal, non-aspirin, users, and users who have been treated with 81 mg, 162 mg or 325 mg aspirin.

For purposes of FIGS. 7-9, Table 6 provides the population that as tested:

TABLE 6

| Methods - Population |
|---|
| Population A, n = 46 |
| Healthy, no previous cardiac events, no aspirin |

TABLE 6-continued

| Methods - Population |
|---|
| Population B |
| Healthy, no previous cardiac events, ±aspirin |
| no aspirin, n = 9 |
| 81 mg aspirin, n = 5 |
| 325 mg aspirin, n = 31 |
| Population C |
| Patients hospitalized with previous cardiac events, +aspirin |
| 81 mg aspirin, n = 42 |
| 162 mg aspirin, n = 33 |
| 325 mg aspirin, n = 31 |

Other assays can also be used in conjunction with the mAb.

Example 11

Clinical Findings in Patients with Coronary Artery Disease or Obesity Using a Urinary 11dhTxB2 Based Competitive ELISA Assay Two patient groups were evaluated for ASA response using 11 dhTxB2/mg urine creatinine in urine. A first group consisted of fifty patients having coronary artery disease (CAD) (herein group A) and the second group consisting of twenty obese female patients having elevated cardiac risk (herein group B). Note that group B patients presented for general surgical procedures. Group A was evaluated peri-procedurally on three different doses of ASA (81 mg) first day and then at day thirty and day sixty when administered 162 and 325 mg ASA respectively. Levels of 11 dhTxB2 are increased in patients that are ASA resistant. Group B patients were screened for ASA response pre-procedure.

Figure 10:
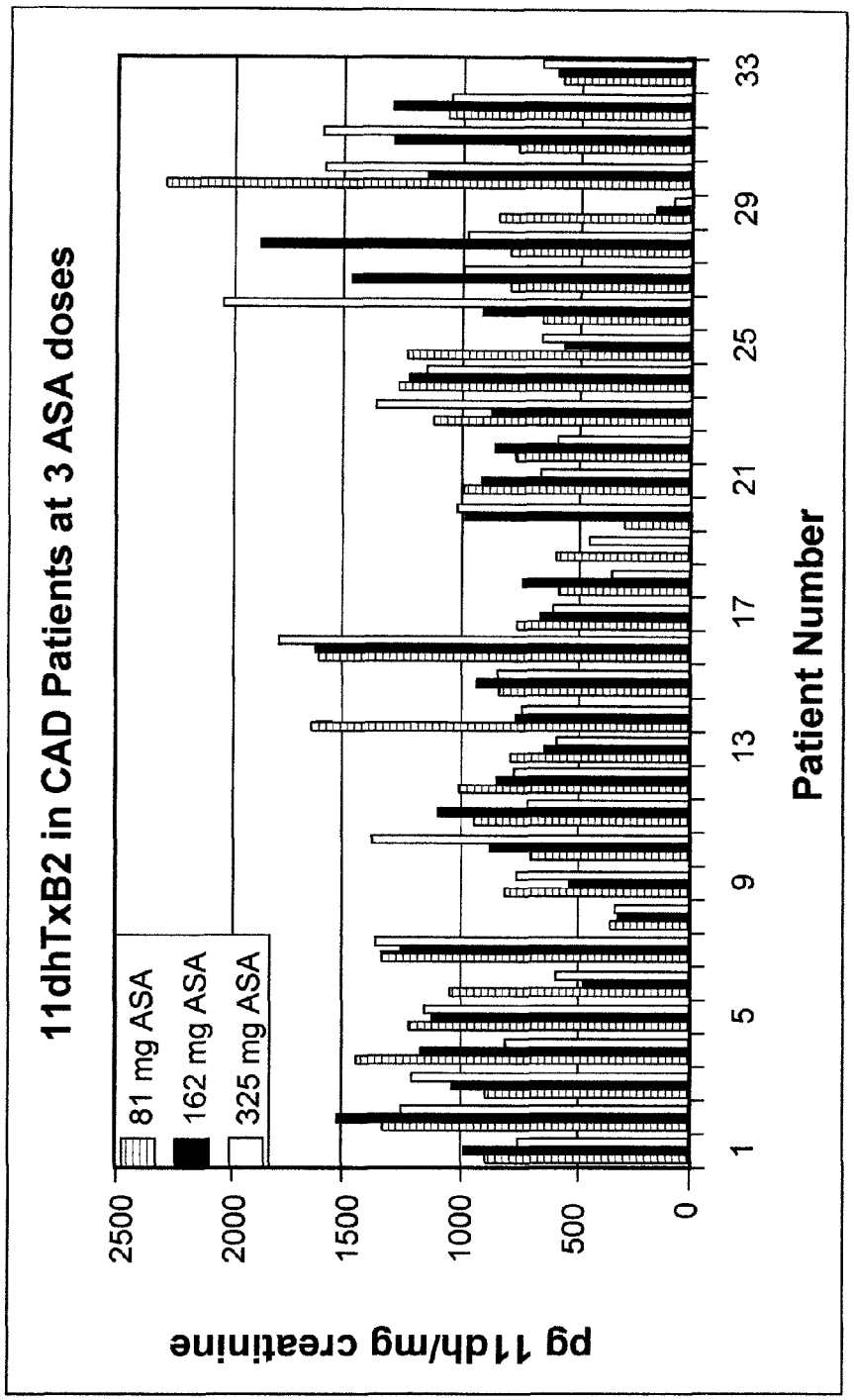
FIG. 10 is a bar graph showing Pg 11dhTxB2/mg creatinine in CAD patients, three doses of ASA were used (81, 162, 325 mg).
Figure 11:
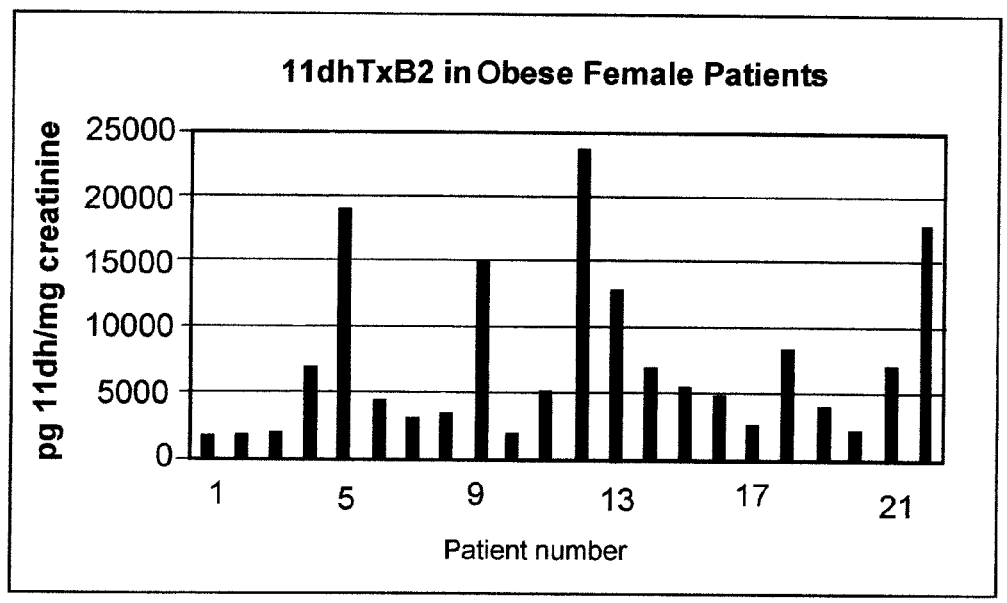
FIG. 11 is a bar graph showing pg 11dhTxB2/mg urine creatinine in female obese patients with high cardiac risk undergoing general surgical procedures, with or without aspirin.

The data for each group is shown in FIGS. 10 (group A) and 11 (group B). The data shows that 11 dh TxB2 is a readily available marker that can quantify insufficient inhibition of TxA2 production by platelets. The test may be suitable for pre-procedural screening to determine the effective dose of ASA on an individual patient basis. The present data shows that TxA2 metabolite testing in urine has great potential to assist clinical decisions as alternatives to anti-platelet therapies.

It is understood for purposes of this disclosure that various changes and modifications may be made to the invention that are well within the scope of the invention. Numerous other changes may be made which will readily suggest themselves to those skilled in the art and which are encompassed in the spirit of the invention disclosed herein.

The list of citations to patents, patent applications and/or publications cited herein are each hereby incorporated by reference for all purposes:

What is claimed is:

1. A method for identifying aspirin response in a subject comprising:
   administering to the subject a first dose of aspirin;
   collecting a urine sample from the subject;
   determining an amount of two thromboxane $A_2$ metabolites in the urine sample, wherein the determining the amount of thromboxane $A_2$ metabolites comprises using a monoclonal antibody capable of binding to 11-dehydro thromboxane $B_2$ and 11-dehydro-2,3-dinor Thromboxane $B_2$;
   normalizing the amount of the two thromboxane $A_2$ metabolites to an amount of a standard protein in the subject's urine to obtain a first thromboxane $A_2$ metabolite/standard protein ratio; and comparing the first thromboxane $A_2$ metabolite/standard protein ratio to a threshold ratio value wherein a thromboxane $A_2$ metabolite/standard protein value below the threshold value indicates aspirin responsiveness in the subject.

2. The method of claim 1 further comprising:
administering to the subject a second dose of aspirin different from the first dose of aspirin, the subject having a first thromboxane $A_2$ metabolite/standard protein ratio above the threshold value, and wherein the first dose and second dose of aspirin are at least 50 mg apart;
collecting a second urine sample from the subject;
determining an amount of the two thromboxane $A_2$ metabolites in the urine sample;
normalizing the amount of the two thromboxane $A_2$ metabolites to an amount of a standard protein in the subject's urine to obtain a second thromboxane $A_2$ metabolite/standard protein ratio; and
comparing the first and second thromboxane $A_2$ metabolite/standard protein ratios;
wherein the subject having substantially the same first and second thromboxane $A_2$ metabolite/standard protein ratio is identified as not responsive to aspirin.

3. The method of claim 2 wherein the first dose and second dose of aspirin are at least 100 mg apart.

4. The method of claim 1 wherein the monoclonal antibody recognizes an epitope common to both 11-dehydro Thromboxane $B_2$ and 11-dehydro-2,3-dinor Thromboxane $B_2$.

5. The method of claim 1, wherein the subject is suffering from or suspected of suffering from thrombotic disease.

6. The method of claim 1, wherein the subject is suffering from or suspected of suffering from cardiovascular disease.

7. The method of claim 1, wherein the subject is suffering from or suspected of suffering from cerebrovascular ischemia.

8. A method for identifying aspirin response in a subject comprising:
administering to the subject a first dose of aspirin;
collecting a blood plasma sample from the subject;
determining an amount of two thromboxane $A_2$ metabolites in the sample, wherein the determining the amount of thromboxane $A_2$ metabolites comprises using a monoclonal antibody capable of binding to 11-dehydro thromboxane $B_2$ and 11-dehydro-2,3-dinor Thromboxane $B_2$;
normalizing the amount of the two thromboxane $A_2$ metabolites to an amount of a standard protein in the subject's plasma to obtain a first thromboxane $A_2$ metabolite/standard protein ratio; and
comparing the first thromboxane $A_2$ metabolite/standard protein ratio to a threshold ratio value wherein a thromboxane $A_2$ metabolite/standard protein value below the threshold value indicates aspirin responsiveness in the subject.

9. The method of claim 8 further comprising:
administering to the subject a second dose of aspirin different from the first dose of aspirin, the subject having a first thromboxane $A_2$ metabolite/standard protein ratio above the threshold value, and wherein the first dose and second dose of aspirin are at least 50 mg apart;
collecting a second plasma sample from the subject;
determining an amount of the two thromboxane $A_2$ metabolites in the plasma sample;
normalizing the amount of the two thromboxane $A_2$ metabolites to an amount of a standard protein in the subject's plasma to obtain a second thromboxane $A_2$ metabolite/standard protein ratio; and
comparing the first and second thromboxane $A_2$ metabolite/standard protein ratios;
wherein the subject having substantially the same first and second thromboxane $A_2$ metabolite/standard protein ratio is identified as not responsive to aspirin.

10. The method of claim 9 wherein the first dose and second dose of aspirin are at least 100 mg apart.

11. The method of claim 8 wherein the monoclonal antibody recognizes an epitope common to both 11-dehydro Thromboxane $B_2$ and 11-dehydro-2,3-dinor Thromboxane $B_2$.

12. The method of claim 8, wherein the subject is suffering from or suspected of suffering from cardiovascular disease.

* * * * *